(12) United States Patent
Pendergast, Jr. et al.

(10) Patent No.: US 10,059,651 B2
(45) Date of Patent: Aug. 28, 2018

(54) SEPARATION PROCESS

(71) Applicants: Dow Global Technologies LLC, Midland, MI (US); Rohm and Haas Company, Philadelphia, PA (US)

(72) Inventors: John G. Pendergast, Jr., Pearland, TX (US); Jacinto Lopez-Toledo, Lake Jackson, TX (US); William G. Worley, Missouri City, TX (US); Stacy W. Hoy, IV, Houston, TX (US); Jacob M. Crosthwaite, Midland, MI (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 0 days.

(21) Appl. No.: 15/522,054

(22) PCT Filed: Oct. 7, 2015

(86) PCT No.: PCT/US2015/054479
§ 371 (c)(1),
(2) Date: Apr. 26, 2017

(87) PCT Pub. No.: WO2016/069227
PCT Pub. Date: Jun. 6, 2016

(65) Prior Publication Data
US 2017/0334829 A1 Nov. 23, 2017

Related U.S. Application Data

(60) Provisional application No. 62/073,406, filed on Oct. 31, 2014.

(51) Int. Cl.
*C07C 67/48* (2006.01)
*C07C 67/54* (2006.01)
*C07C 29/84* (2006.01)
*C07C 69/54* (2006.01)

(52) U.S. Cl.
CPC .............. *C07C 67/54* (2013.01); *C07C 29/84* (2013.01); *C07C 69/54* (2013.01)

(58) Field of Classification Search
CPC ......... C07C 67/54; C07C 29/82; C07C 69/54; C07C 31/04; B01D 3/007; B01D 3/143; B01D 3/36
See application file for complete search history.

(56) References Cited

U.S. PATENT DOCUMENTS

| | | | |
|---|---|---|---|
| 4,249,019 A | 2/1981 | Tamura et al. | |
| 4,518,462 A * | 5/1985 | Aoshima | C07C 67/54 203/15 |
| 4,518,796 A | 5/1985 | Aoshima et al. | |
| 5,028,735 A | 7/1991 | Segawa et al. | |
| 5,435,892 A | 7/1995 | Miyazaki et al. | |
| 5,892,102 A | 4/1999 | Mikami et al. | |
| 5,969,178 A | 10/1999 | Okamoto et al. | |
| 6,040,472 A | 3/2000 | Yamamatsu et al. | |
| 6,107,515 A | 8/2000 | Yamaguchi et al. | |
| 6,680,405 B1 | 1/2004 | Munetou et al. | |
| 2013/0072712 A1 | 3/2013 | Kawamoto et al. | |

FOREIGN PATENT DOCUMENTS

JP 2582127 B2 2/1997
JP 3819419 B2 9/2006

* cited by examiner

*Primary Examiner* — Yevgeny Valenrod
*Assistant Examiner* — Blaine G Doletski
(74) *Attorney, Agent, or Firm* — Edward L. Brant

(57) ABSTRACT

The azeotrope, or near azeotrope, of methanol and MMA is separated via extractive distillation using an extractive distillation solvent comprising cyclohexanone.

13 Claims, 1 Drawing Sheet

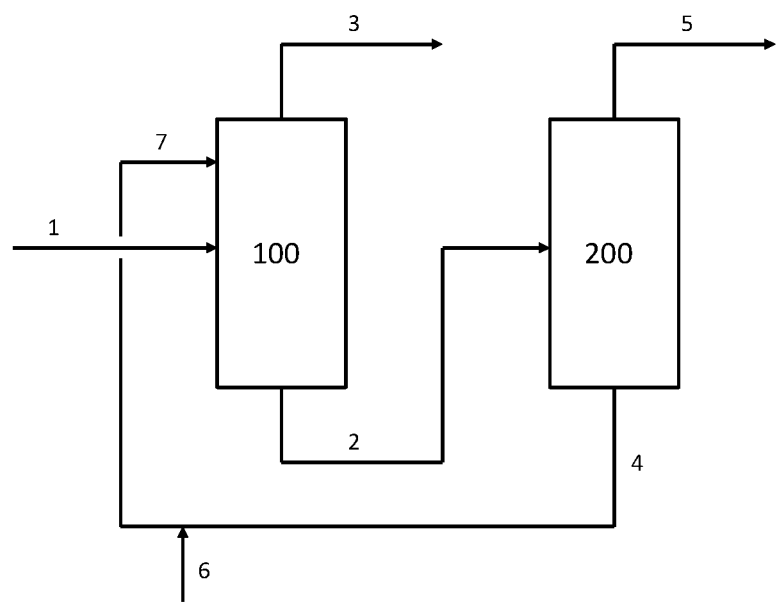

US 10,059,651 B2

SEPARATION PROCESS

BACKGROUND OF THE INVENTION

The invention relates to a process for the separation of methanol and methylmethacrylate (MMA).

Methanol is used in the manufacture of MMA. One process for making MMA involves the oxidative esterification of methacrolein (MAL) with methanol. In the manufacturing process, mixtures of MMA and methanol are formed. It is difficult to separate the components from these mixtures, as MMA and methanol form an azeotrope or a "near azeotrope," also referred to as a "tangent pinch." This means that the components cannot be separated by conventional distillation, and that special measures are needed to accomplish the separation.

JP 03819419 B2 describes a methanol recovery column where the methanol and methacrolein are separated from MMA in a distillation column with no other separating agents added. The overhead composition is limited by the azeotropic composition (11 wt % of MMA in methanol). While the azeotropic composition can be approached by using a large number of trays and/or a high reflux ratio, the MMA composition in the overheads cannot be less than the azeotropic composition. This is undesirable as the MMA is the desired product, and sending it back to the reactor requires larger equipment and, more importantly, provides the opportunity for the valuable product to react further to by-products, thereby lowering the MMA yield.

U.S. Pat. No. 4,518,462 describes the removal of methanol from MMA using a $C_6$-$C_7$ saturated hydrocarbon, e.g., hexane, cyclohexane, heptane, methyl cyclopentane or dimethylpentane, as an entrainer. No water is added to the overheads decanter, so the phases split into hydrocarbon-rich and methanol-rich layers. One of the drawbacks of this approach is the limited ability to dry the recycle stream. In addition, in order to reduce the MMA to low levels in the recycle stream, a large amount of entrainer is required, resulting in high energy usage and a large and expensive distillation column.

U.S. Pat. Nos. 5,028,735, 5,435,892, and JP 02582127 B2 describe a similar entrainer process where either sufficient water is in the feed or water is added to the overhead decanter to form an organic and aqueous layer. In this case, essentially all of the hydrocarbon entrainer resides in the organic layer. The aqueous layer can be sent to a drying column to remove water from the recycle stream; however, large amounts of hexane are still required to minimize MMA in the recycle stream. For example, U.S. Pat. No. 5,028,735 describes an entrainer process using hexane as the entrainer with hexane usage of at least 17-fold the water content of the feed and 3-fold the methanol in the feed.

U.S. Pat. No. 6,680,405, uses methacrolein as an entrainer. While the azeotrope composition was broken, it resulted in only a minor improvement, namely 7.4% MMA in the recycle stream.

In view of the deficiencies of the prior art, it would be desirable to have an improved method for the separation of methanol and MMA.

SUMMARY OF THE INVENTION

The process of the invention is such a process comprising separating methanol from MMA via extractive distillation using an extractive distillation solvent comprising cyclohexanone.

Surprisingly, cyclohexanone provides an improved separation compared to the methods of the prior art.

BRIEF DESCRIPTION OF THE DRAWINGS

The FIGURE is a process block flow diagram of an embodiment of the invention.

DETAILED DESCRIPTION OF THE INVENTION

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "ppmw" means part per million by weight.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

The process of the invention employs methanol, MMA, and cyclohexanone. Each of these materials is well-known and commercially available. The methanol and MMA are present together as a mixture in an input stream to the process. Mixtures comprising methanol and MMA are produced by various chemical processes including, for example, the oxidative esterification of MAL to produce MMA. The oxidative esterification process is well known. See, e.g., U.S. Pat. Nos. 5,969,178, 6,107,515, 6,040,472, 5,892,102, 4,249,019, and 4,518,796. MMA can also be produce via a 3-step process comprising: (a) hydroformylation of ethylene with hydrogen and CO to produce propionaldehyde; (b) reacting propionaldehyde with formaldehyde to produce MAL; and (c) oxidatively esterifying MAL using methanol and oxygen to produce MMA. One purpose of the process of the invention is to separate MMA from methanol.

Cyclohexanone is widely commercially available and is employed in the process of the invention as an extractive distillation solvent. The amount of cyclohexanone employed advantageously is sufficient to provide a good separation of methanol and MMA. In one embodiment of the invention, the molar ratio of cyclohexanone to MMA fed to the first distillation column is from 3:1 to 10:1, preferably from 6:1 to 8:1.

The FIGURE depicts a preferred embodiment of the invention. For the sake of brevity in description, The FIGURE does not include auxiliary equipment such as pumps, reboilers, condensers, etc. as one skilled in the art will be well aware of design considerations related to these. Feed stream 1 comprises a mixture of methanol and MMA. In one embodiment of the invention, the mixture is an effluent stream from a process wherein MMA is produced by the oxidative esterification of MAL. In that process, which is well-known to those skilled in the art, MAL is contacted with an oxygen-containing gas and methanol over a catalyst to produce MMA. The reactor effluent stream 1 comprises MMA, unreacted methanol, and by-products. Stream 1 is fed into distillation column 100. Stream 7, an extraction solvent recycle stream, is also fed to column 100.

Stream 3 is the overhead stream from column 100, and it comprises mainly methanol. Stream 2 is a bottoms stream from column 100. It is fed to distillation column 200, where it is distilled to remove the extraction solvent as a bottoms stream 4 from the product, which is taken overhead in stream 5. Stream 5 is the overhead stream from column 200, and comprises mainly MMA and water. Stream 5 is sent to a product recovery zone for further purification. Bottoms stream 4 from column 200 comprises mainly the extraction solvent. Stream 6 comprises makeup solvent, i.e., cyclohexanone. Stream 4 is combined with stream 6 to form stream 7, which is sent to column 100 in order to recycle the solvent.

In one embodiment of the invention, stream 7 is introduced into column 100 above the feed point of stream 1. For example, stream 1 can be introduced near the vertical center, e.g., near the center tray, of column 100, and stream 7 can be introduced at from 2 to 5 trays below the top of column 100. In one embodiment of the invention, stream 2 is introduced near the center of column 200.

In one embodiment of the invention, purge streams are taken from the process to avoid the accumulation of solids and heavies. For the purposes of the invention, the term "heavies" means any compound having a boiling point higher than that of MMA. For example, in The FIGURE, a heavies purge stream (not shown) can be taken from the bottoms stream 4 of the second distillation column 200. In such an embodiment, stream 6 is a solvent makeup stream that provides extraction solvent to replace any extraction solvent lost via the purge stream or other means.

In one embodiment of the invention, rather than, or in addition to, having a purge stream, heavies can be removed from the extraction solvent in an optional third distillation column. For example, in the context of The FIGURE, all or part of bottoms stream 4 from column 200 can be fed to an optional third column (not shown) in which the extraction solvent is distilled to remove heavies. The distilled solvent is then sent to the first column.

The distillation columns can be operated at pressures and temperatures suitable for achieving the desired separations. For example, the absorber column, or first column, performing the extractive distillation of the MMA, can be operated at any suitable pressure. Advantageously, the pressure in the absorber column is atmospheric pressure or slightly above atmospheric pressure. This allows the overhead material, which is predominantly methanol and other lighter components, to be condensed with normal cooling water or by air coolers. The second column, recovering the MMA from the extraction solvent, is advantageously operated at a pressure that is below atmospheric pressure. This is done primarily due to the fact that MMA is a reactive molecule, and exposure to a high temperature promotes fouling by polymerization of the MMA molecule. Thus, by running the second column at from 250 to 700 mmHg, preferably 500 to 650 mmHg, absolute pressure, the temperature of the recovered MMA product, e.g., the temperature at the top of the second column, may be maintained well below the temperature where the onset of polymerization is considered to be problematic. The bottom of the second column can be maintained at from 130 to 160° C., or from 140 to 150° C., allowing the solvent to be recovered using a low to moderate pressure heating medium. Similarly, the third column, if employed, can be operated at conditions readily discernable to those skilled in the art. As known to those skilled in the art, the distillation temperature and pressure are linked to each other based on the composition of the material being separated.

A polymerization inhibitor can be employed in the process when the product is a polymerizable compound. A wide variety of inhibitors are known and commercially available. Examples of inhibitors include hydroquinone (HQ), phenothiazine (PTZ), the methyl ester of hydroquinone (MEHQ), 4-hydroxy-2 2 6 6-tetramethylpiperidine-n-oxyl (4-hydroxy TEMPO, or 4HT), methylene blue, alkyl-arylphenylenediamine, copper salicylate, copper dialkyldithiocarbamates, and the like.

The distillation of the invention may be conducted in any suitable equipment. For example, distillation can be conducted in towers with internals comprising trays and/or packing. Process design details, including the choice of equipment and materials of construction, are within the capabilities of one of ordinary skill in the art.

The product of the process of the invention is MMA that has been separated from methanol. It is likely that some methanol will still be present in the purified MMA. In various embodiments of the invention, at least 95%, at least 99%, or at least 99.5% by weight, of the MMA in the input stream is recovered. In various embodiments of the invention, the MMA produced by the process of the invention contains less than 1,000 ppmw methanol by weight, or less than 500 ppmw methanol. The process of the invention advantageously is able to provide to the reactor a recycle stream containing less than 1 wt. % MMA or less than 7500 ppmw, or less than 5000 ppmw, or less than 2500 ppmw, or less than 1000 ppmw, or less than 500 ppmw.

Specific Embodiments of the Invention

The following example is given to illustrate the invention and should not be construed as limiting its scope.

EXAMPLE 1

A process as shown in The FIGURE is simulated, except that stream 6 is not included. The temperature, pressure, density and flow rates are shown for each of streams 1 through 5 and 7 in Table 1. The process is simulated using Aspen Plus™ Version 8.0, which is commercially available from Aspen Technologies, Inc. The separations process, absorber (first column) and stripper (second column), are modeled using rigorous stage separation blocks, designated as RADFRAC in the Aspen simulation software nomenclature. The physical properties are modeled using an activity coefficient model developed with normally accepted best practices within the Aspen simulation package. The interaction parameters required to accurately reflect the behavior of the vapor/liquid equilibrium are obtained by experimental binary data to validate and improve the interaction parameters for the vapor liquid equilibrium, as well as for the liquid/liquid equilibrium.

The following abbreviations are used in Table 1: MEOH—methanol; MEFORM—methyl formate; MA—methacrolein; H2O—water; MMA—methyl methacrylate; and CHEX cyclohexanone.

TABLE 1

Stream data for Ex. 1

|  | FEED 1 | OHD-1 3 | SOLVENT 7 | REC-SOL 4 | ENT-BTMS 2 | MMA-PROD 5 |
|---|---|---|---|---|---|---|
| Temperature ° C. | 84.4 | 62.9 | 25 | 148.7 | 102 | 70.6 |
| Pressure bar | 2 | 1.01 | 1.2 | 0.87 | 1.03 | 0.8 |
| Density lb/cuft |  | 47.493 | 58.826 | 51.653 | 54.857 | 56.303 |
| Mass Flow kg/hr |  |  |  |  |  |  |
| H2O | 668.0 | 0.0 |  |  | 668.0 | 668.0 |
| MEOH | 6207.9 | 6044.3 |  |  | 163.6 | 163.6 |
| MEFORM | 22.8 | 22.8 |  |  |  |  |
| MA | 716.1 | 715.7 |  |  | 0.3 | 0.3 |
| MMA | 2385.2 | 1.0 |  | 0.0 | 2384.2 | 2384.2 |
| CHEX | 0.0 | 0.6 | 13668.5 | 13667.9 | 13667.9 |  |
| Mass Frac |  |  |  |  |  |  |
| H2O | 0.067 | 5 PPM |  |  | 0.0 | 0.208 |
| MEOH | 0.621 | 0.947 |  |  | 0.0 | 0.051 |
| MEFORM | 0.002 | 0.002 |  |  |  |  |
| MA | 0.072 | 0.051 |  |  | 20 PPM | 102 PPM |
| MMA | 0.239 | 146 PPM |  | 0.00 | 0.1 | 0.741 |
| CHEX |  | 96 PPM | 1.0 | 1.00 | 0.8 |  |
| Mole Flow kmol/hr |  |  |  |  |  |  |
| H2O | 37.08 | 0.00 | 0.00 | 0.00 | 37.08 | 37.08 |
| MEOH | 193.74 | 188.64 | 0.00 | 0.00 | 5.10 | 5.10 |
| MEFORM | 0.38 | 0.38 | 0.00 | 0.00 | 0.00 | 0.00 |
| MA | 10.22 | 10.21 | 0.00 | 0.00 | 0.00 | 0.00 |
| MMA | 23.82 | 0.01 | 0.00 | 1.03 | 23.81 | 23.81 |
| CHEX | 0.00 | 0.00 | 1.42 | 1.42 | 1.42 | 0.00 |
| Mole Frac |  |  |  |  |  |  |
| H2O | 0.140 | 9 PPM |  | trace | 0.2 | 0.562 |
| MEOH | 0.730 | 0.947 |  | trace | 0.0 | 0.077 |
| MEFORM | 0.001 | 0.002 |  | trace | trace | trace |
| MA | 0.039 | 0.051 |  | trace | 23 PPM | 71 PPM |
| MMA | 0.090 | 49 PPM |  | trace | 0.1 | 0.361 |
| CHEX |  | 33 PPM | 1.0 | 1.0 | 0.7 | 1 PPM |

Surprisingly, only 146 ppm MMA are in the overheads stream of the first column, showing the effectiveness of the separation.

What is claimed is:

1. A process comprising separating methanol from (MMA) methylmethacrylate via extractive distillation using an extractive distillation solvent comprising cyclohexanone.

2. The process of claim 1 wherein: (a) a feed stream comprising MMA and methanol is fed to a first distillation column; (b) a stream comprising cyclohexanone solvent is fed to the first column; (c) a first bottoms stream is taken from the first column, the first bottoms stream comprising primarily MMA and solvent; and (d) a first overhead stream is taken from the first column, the first overhead stream comprising primarily methanol.

3. The process of claim 2 further comprising the steps: (e) at least a portion of the first bottoms stream is fed to a second distillation column; (f) a second bottoms stream is taken from the second column, the second bottoms stream comprising primarily solvent; (g) a second overhead stream is taken from the second column, the second overhead stream comprising primarily MMA; and (h) at least part of the second bottoms stream is recycled to the first distillation column.

4. The process of claim 2 wherein the molar ratio of cyclohexanone to MMA fed to the first distillation column is from 3:1 to 10:1.

5. The process of claim 2 wherein the pressure in the first column is at least atmospheric pressure, measured at the uppermost vapor outlet of the column.

6. The process of claim 2 wherein the pressure in the second column is below atmospheric pressure, measured at the uppermost vapor outlet of the column.

7. The process of claim 2 wherein the pressure in the second column is from 250 to 700 mmHg.

8. The process of claim 2 wherein the second column is equipped with a reboiler having a process side and a utility side, and wherein the process side reboiler temperature is from 130 to 160° C.

9. The process of claim 2 wherein the first bottoms stream contains up to 8 weight parts methanol per 100 parts of MMA.

10. The process of claim 2 further comprising (i) distilling in a third distillation column at least a portion of the second bottoms stream to remove heavies before the second bottoms stream is recycled to the first distillation column.

11. The process of claim 2 wherein the molar ratio of cyclohexanone to MMA fed to the first distillation column is from 6:1 to 8:1.

12. The process of claim 2 wherein the pressure in the second column is from 500 to 650 mmHg.

13. The process of claim 2 wherein the second column is equipped with a reboiler having a process side and a utility side, and wherein the process side reboiler temperature is from 140 to 150° C.

\* \* \* \* \*